United States Patent [19]
Hurwitz et al.

[11] Patent Number: 5,959,870
[45] Date of Patent: Sep. 28, 1999

[54] REAL-TIME OPTIMIZATION FOR MIX BEDS

[75] Inventors: Michael Jack Hurwitz; Richard Edgar Ackermann, both of San Diego, Calif.

[73] Assignee: Gamma-Metrics, San Diego, Calif.

[21] Appl. No.: 09/026,632

[22] Filed: Feb. 20, 1998

[51] Int. Cl.$^6$ .................................................. G06F 17/00
[52] U.S. Cl. .................. 364/479.09; 198/508; 366/153.2
[58] Field of Search ....................... 364/479.09; 198/508; 366/153.2, 8, 17, 16

[56] References Cited

U.S. PATENT DOCUMENTS

| | | | |
|---|---|---|---|
| 662,063 | 11/1900 | Edison | 198/508 |
| 677,677 | 7/1901 | Messiter | 198/508 |
| 3,233,877 | 2/1966 | Kelly | 366/153.2 |
| 3,606,954 | 9/1971 | Mayer | 198/508 |
| 3,609,316 | 9/1971 | Brosset et al. | 364/479.09 |
| 4,582,992 | 4/1986 | Atwell et al. | |
| 4,744,459 | 5/1988 | Ryan | 198/508 |
| 5,396,071 | 3/1995 | Atwell et al. | |
| 5,732,115 | 3/1998 | Atwell et al. | |

FOREIGN PATENT DOCUMENTS 914764  3/1982  U.S.S.R. .

OTHER PUBLICATIONS

Ahrens, "Latest Developments in Circular Mix Bed Technology" Bulk Solids Handling, vol. 17, No. 2, Apr./Jun. 1997 pp. 257–263.

Primary Examiner—William E. Terrell
Assistant Examiner—Khoi H. Tran
Attorney, Agent, or Firm—Edward W. Callan

[57] ABSTRACT

During the building of a mix bed of variable bulk materials, from which slices of the bulk materials are reclaimed from time to time, a computer processes composition analyses and quantity measurements to provide a real time data base of the current aggregate composition of the bulk materials in respective sectors of the mix bed and further processes current composition analyses and current quantity measurements with the real time data base to predict an aggregate composition of the bulk materials in the respective sectors of the mix bed when the respective sectors are reclaimed. When the aggregate-composition predictions indicate that stacking of a given delivered bulk material onto a given location of the mix bed would cause a given sector of the mix bed to be of an undesired aggregate composition when the given sector of the mix bed is reclaimed, the computer causes stacking of the given delivered bulk material onto the given location of the mix bed to be omitted and further causes at least one corrective bulk material to be stacked onto the given location of the mix bed subsequent to said omission in order to cause the given sector of the mix bed to be of a desired aggregate composition when the given sector of the mix bed is reclaimed.

36 Claims, 5 Drawing Sheets

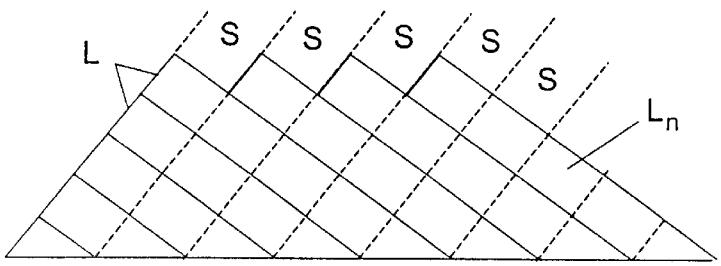
FIG. 6
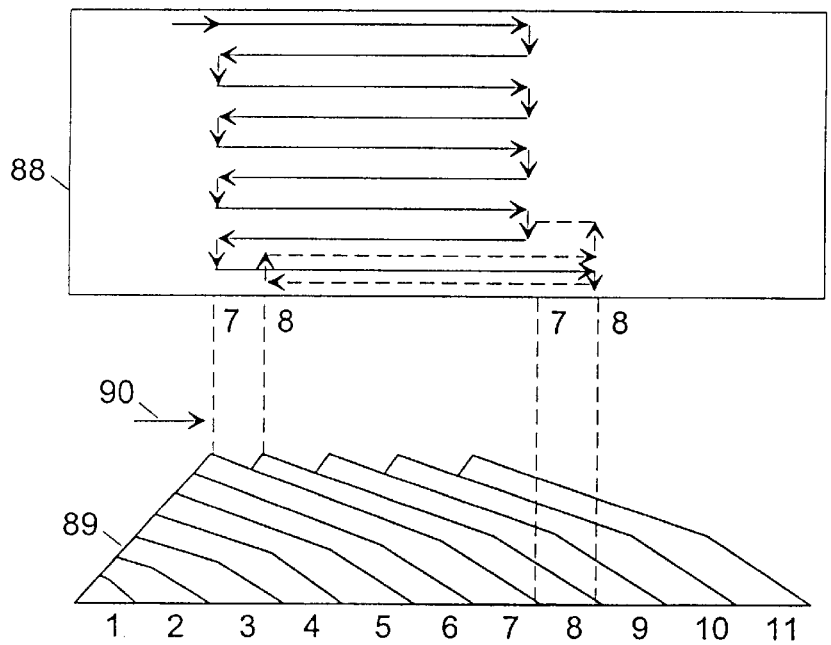
FIG. 7A
PRIOR ART
FIG. 7B
PRIOR ART
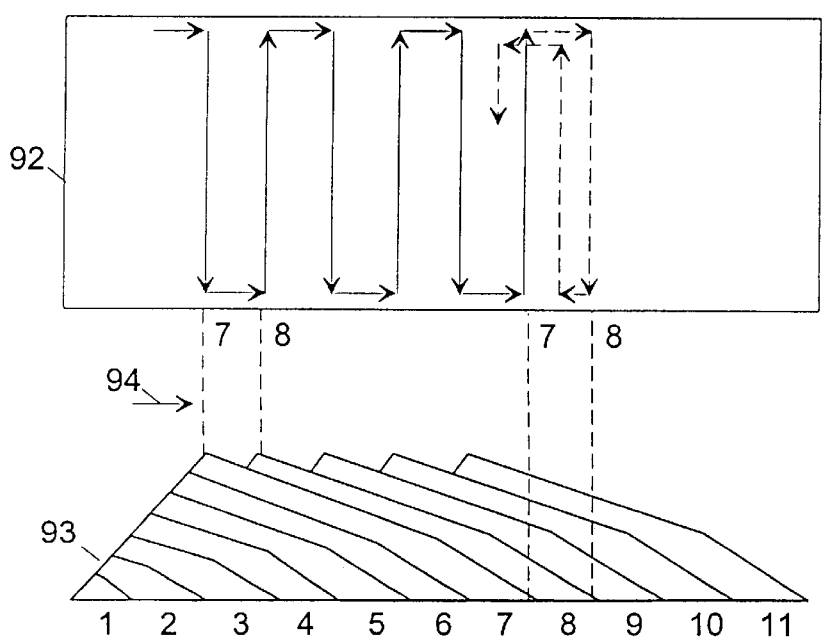
FIG. 8A
PRIOR ART
FIG. 8B
PRIOR ART

REAL-TIME OPTIMIZATION FOR MIX BEDS

BACKGROUND OF THE INVENTION

The present invention generally pertains to building mix beds of variable bulk materials, from which slices of the bulk material are reclaimed from time to time, and is particularly directed to improved systems, methods and computer readable storage media for determining the compositions of the mix beds as they are being built and for the stacking of the bulk materials onto the mix bed in such a manner as to build a mix bed having a desired composition throughout the mix bed. Variable bulk materials include different types of bulk materials and/or bulk materials of a given type having variable compositions.

Mix beds, also known as blending beds, are widely used in the cement industry and other industries, such as coal processing, mining, grain and fertilizer, to reduce variability in the bulk materials when processed, as well as to provide a stockpile for processing when the material production or material delivery systems are halted. Although mix beds are sometimes used to homogenize material delivered from a single source, mix beds frequently are used to homogenize different materials respectively delivered from different sources, such as mixtures of limestone and clay for use by cement plants and mixtures of high and low sulfur coal for use by power plants. It is an object of the present invention to reduce variability throughout the mix bed to such an extent that further homogenization will not be required.

Mix beds are composed of many layers of bulk material. FIG. 1 shows a typical longitudinal mix bed 10 in which a stacker 12 moves back and forth along the ridge 14 of the mix bed 10 and stacks many layers of variable bulk materials. The bulk material is delivered to the stacker 12 from a selected source of bulk materials by a conveyor 15. FIG. 2 is a vertical sectional view of the mix bed 10 taken normal to the movement of the stacker 12. The bulk material stacked on the ridge 14 of the mix bed 10 by the stacker 12 tumbles down the faces of the mix bed 10 to thereby distribute itself in chevrons, as shown in FIG. 2; whereby the respective layers L become thinner as the height of the mix bed 10 increases, as also shown in FIG. 2. While one mix bed 10 is being built, slices of bulk materials are being reclaimed by a reclaimer 16 from a previously built mix bed 10'. The reclaimer 16 removes the bulk material from the mix bed 10' while advancing from one end of the mix bed 10' to the other. Reclaimers 16 typically reclaim bulk material from a mix bed 10 at an angle with respect to the stacked layers L that is inclined to be equal to or slightly larger than the angle of repose of the bulk material. By this process, material from a large number of layers L is simultaneously recovered from the mix bed 10' and thereby blended to be of an aggregate composition combining the respective compositions of the blended layers L. Normally, the respective compositions of the layers are selected to produce the desired aggregate composition of the entire mix bed 10. Since the layers are independent from one another, variations are mainly random, and the reclaiming process recovers a portion of a large number of layers L simultaneously, with the homogenization effect being approximately proportional to the square root of the number of layers L intersected by the reclaimer.

FIG. 3 shows a continuous-mode circular mix bed 20, that is built by a rotating stacker 22 continuously stacking bulk material onto a ridge 23 that is thereby continuously extended toward a continuously extending blending tail 24 at one end of the mix bed 20 while bulk material is being continuously reclaimed from the other end 25 of the mix bed 20 by a rotating reclaimer 26; whereby there is no need to move the stacker 22 and the reclaimer 26 from one mix bed 20 to another. Both the stacker 22 and the reclaimer 26 rotate in the same circular direction 27 about a common central axis 28. The bulk material is delivered to the stacker 22 from a selected source of bulk material by a conveyor 29. The bulk material stacked onto the ridge 23 by the stacker 22 tumbles down the faces of the mix bed 20 to thereby distribute itself in layers, as shown in FIG. 2. The stacker 22 moves back and forth in the circular direction 27 along the ridge 23, typically at a fixed elevation above the ridge line, to make overlapping layers, as shown in FIG. 4, which is a vertical sectional view of the mix bed 20 taken in alignment with the circular direction of movement 27 of the stacker 22. The respective layers L are shown to be of an arbitrary constant size but are physically distinguishable from each other only where there is a variation in the bulk material being stacked onto the ridge 23. In the prior art, the length of the blending tail 24 is determined by the homogenization requirements for the bulk material. As shown in FIG. 4 the layers L of the circular-mode mix bed 20 are stacked in an inclined fashion with the angle of the incline chosen to yield the desired tail length but being equal to or less than the angle of repose of the bulk material. These layers L have a length determined by the incline angle and the finished height of the ridge 23. The reclaimer 26 reclaims the bulk material from the mix bed 20 in the same manner as the reclaimer 16 reclaims bulk from the mix bed 10', as described above with reference to FIG. 1.

In order to build a mix bed having a desired aggregate composition, predetermined quantities of selected bulk materials are delivered to the mix bed for stacking by the stacker in accordance with a schedule so that the respective slices of bulk material that are reclaimed from the mix bed in accordance with the homogenizing capability of the mix bed are of a desired aggregate composition within an acceptable range of aggregate compositions. Sometimes, however, due to equipment failure or other problems, such as variations in the composition of a particular selected bulk material, one or more of the selected bulk materials are not immediately available, thereby making it impossible to build the mix bed in accordance with a schedule. If the mix bed building process is not interrupted when this condition occurs, it is possible for various sectors S of the mix bed to have an undesired aggregate composition. A sector is a three-dimensional lateral segment of arbitrary size and extending between the top and the bottom and toward the sides of the mix bed 10, 20 in an orientation that is vertical, as shown in FIG. 4, and approximately normal to the direction of advancement of the reclaimer 16, 26. In a circular mix bed 20, a sector S may also be delineated by radii and a portion of the mix bed circumference.

Various on-line analyzers and/or sampling techniques are used to determine the aggregate composition of a mix bed as the mix bed is being built so that an undesired aggregate composition of a given sector S of the mix bed can be recognized and then corrected. For example a bulk material analyzer, such as an analyzer utilizing prompt gamma-ray neutron activation analysis (PGNAA), is disposed about a conveyer delivering bulk material to the stacker to analyze the composition of the bulk material being delivered to the stacker; and the quantity of the bulk material of such composition that is being delivered to the stacker is measured gravimetrically by means such as a scales disposed within the conveyor assembly.

A disadvantage incident to building continuous-mode circular mix beds 20 when compared to building longitudinal mix beds 10 has been an inability to correct an undesired aggregate composition of an individual sector S located between the top of the blending tail 24 and the other end 25 of the circular-mode mix bed 20 without having to interrupt the continuous building of the mix bed 20. Longitudinal mix beds 10 are considered to be of a consistent aggregate composition between, but not at, the end portions because they are constructed from hundreds of thin horizontal layers covering the full length of the mix bed. An undesired aggregate composition of a longitudinal mix bed 10 can be adjusted at any time simply by adding additional layers of a corrective bulk material; whereas bulk material is added to a continuous-mode circular mix bed 20 only on the blending tail 24 such that those sectors S of an undesired aggregate composition located between the top of the blending tail 24 and the other end 25 of a continuous-mode mix bed 20 where the bulk material is being reclaimed can no longer be corrected during the continuous mode of operation and can be corrected only by adding corrective material to those sectors after the continuous building of the mix bed 20 has been interrupted. For this reason many operators of circular mix beds have chosen to operate them in a batch mode that permits correction in the same manner as in a longitudinal mix bed, wherein corrective bulk material is added uniformly over a batch that caused the mix bed to be of an undesired aggregate composition.

One prior art technique for correcting aggregate-composition irregularities detected in a continuous-mode circular mix bed while building the mix bed, as described by Ahrens, "Latest Developments in Circular Mix Bed Technology", Bulk Solids Handling, Vol. 17, No. 2, April/June 1997, pp. 257–263, is to sample and analyze the composition of the different layers of the circular mix bed as the circular mix bed is being built and to stack an overlapping layer of corrective bulk material when it is determined from such analysis that the layers of bulk material being overlapped are not of a predetermined aggregate composition. However, such technique does not appear to be applicable for correcting aggregate-composition irregularities detected in given sectors S of the mix bed 20 while building the mix bed 20.

SUMMARY OF THE INVENTION

The present invention provides improved systems and methods for use in correcting aggregate-composition irregularities detected in given sectors of the mix bed while building the mix bed.

In one aspect, the present invention provides a system for building a mix bed of variable bulk materials, from which slices of the bulk materials are reclaimed from time to time, comprising means for building a mix bed composed of many layers of variable bulk materials by stacking delivered variable bulk materials onto the mix bed at different locations in accordance with a schedule; means for analyzing the composition of the bulk materials being delivered for stacking onto the mix bed; means for measuring the quantities of the bulk materials being delivered for stacking onto the mix bed; means for correlating the composition analyses and the quantity measurements with the different locations to which the bulk materials are being delivered for stacking; and means adapted for processing the composition analyses and the quantity measurements with the location correlations to predict, in accordance with the compositions and quantities of the bulk materials being delivered for stacking onto the mix bed, an aggregate composition of the bulk materials in respective sectors of the mix bed when said respective sectors are reclaimed. Such system may further comprise means adapted for responding to said aggregate-composition predictions by causing stacking of a given delivered bulk material onto a given location of the mix bed to be omitted when it is predicted that stacking of said given delivered bulk material onto said given location of the mix bed would cause a given sector of the mix bed including said given delivered bulk material delivered onto said given location to be of an undesired aggregate composition when said given sector of the mix bed is reclaimed. Such system may also further comprise means adapted for responding to said undesired-aggregate-composition prediction by causing at least one corrective bulk material to be stacked onto said given location of the mix bed subsequent to said omission in order to cause said given sector of the mix bed to be of a desired aggregate composition when said given sector of the mix bed is reclaimed.

Accordingly, aggregate-composition irregularities in one or more given sectors of a mix bed can be corrected selectively without interrupting the continuous building of the mix bed.

In another aspect, the present invention provides a system for building a mix bed of variable bulk materials, from which slices of the bulk materials are reclaimed from time to time, comprising means for building a mix bed composed of many layers of variable bulk materials by stacking delivered variable bulk materials onto the mix bed at different locations in accordance with a schedule; means for analyzing the composition of the bulk materials being delivered for stacking onto the mix bed; means for measuring the quantities of the bulk materials being delivered for stacking onto the mix bed; means for correlating the composition analyses and the quantity measurements with the different locations to which the bulk materials are being delivered for stacking; and means adapted for processing the composition analyses and the quantity measurements with the location correlations to provide a real time data base of the current composition of the bulk materials in respective sectors of the mix bed. Such system may further comprise means adapted for processing current composition analyses and current quantity measurements with current location correlations and the real time data base to predict, in accordance with the compositions and quantities of the bulk materials being delivered for stacking onto the mix bed, an aggregate composition of the bulk materials in said respective sectors of the mix bed when said respective sectors are reclaimed.

The present invention further provides methods for building a mix bed of variable bulk materials, from which slices of the bulk materials are reclaimed from time to time, said methods corresponding respectively to the operation of the above-described systems provided by the present invention.

In still another aspect, the present invention provides a system for building a mix bed of variable bulk materials, from which slices of the bulk materials are reclaimed from time to time, comprising a stacker for feeding bulk materials and for depositing the fed bulk materials at a plurality of different locations of a mix bed to sequentially form a plurality of stacked layers of bulk materials across the mix bed; a stacker locator for providing a location signal indicating the location at which the stacker is depositing the bulk material; a composition analyzer for determining a composition of the bulk materials being fed by the stacker and for providing a composition signal indicating said determined composition; a quantity measurement system for measuring a quantity of the bulk materials being fed by the stacker and for providing a quantity signal indicating said measured quantity; and a computer coupled to the stacker locator, the composition analyzer and the quantity measurement system for receiving the location signal, the composition signal and the quantity signal, wherein the computer is adapted for processing the location signal, the composition signal and the quantity signal to correlate the location at which the stacker deposits the bulk material with the composition and quantity of the bulk material deposited at said location and to calculate a predicted aggregate composition of the bulk materials within a selected sector of the mix bed formed by deposit of bulk material at said location.

The present invention also provides a system for use in a method of building a mix bed composed of many layers of variable bulk materials, from which slices of the bulk materials are reclaimed from time to time, said method including the steps of building a mix bed composed of many layers of variable bulk materials by stacking delivered variable bulk materials onto the mix bed at different locations in accordance with a schedule; analyzing the composition of the bulk materials being delivered for stacking onto the mix bed; measuring the quantities of the bulk materials being delivered for stacking onto the mix bed; and correlating the composition analyses and the quantity measurements with the different locations to which the bulk materials are being delivered for stacking, said system comprising means adapted for processing the composition analyses and the quantity measurements with the location correlations to predict, in accordance with the compositions and quantities of the bulk materials being delivered for stacking onto the mix bed, an aggregate composition of the bulk materials in respective sectors of the mix bed when said respective sectors are reclaimed; and means adapted for responding to said aggregate-composition predictions by causing stacking of a given delivered bulk material onto a given location of the mix bed to be omitted when it is predicted that stacking of said given delivered bulk material onto said given location of the mix bed would cause a given sector of the mix bed including said given delivered bulk material delivered onto said given location to be of an undesired aggregate composition when said given sector of the mix bed is reclaimed.

The present invention still further provides a computer readable storage medium for use in a computer used in a method of building a mix bed composed of many layers of variable bulk materials, from which slices of the bulk materials are reclaimed from time to time, said method including the steps of building a mix bed composed of many layers of variable bulk materials by stacking delivered variable bulk materials onto the mix bed at different locations in accordance with a schedule; analyzing the composition of the bulk materials being delivered for stacking onto the mix bed; measuring the quantities of the bulk materials being delivered for stacking onto the mix bed; and correlating the composition analyses and the quantity measurements with the different locations to which the bulk materials are being delivered for stacking, wherein the storage medium is configured so as to cause the computer to process the composition analyses and the quantity measurements with the location correlations to predict, in accordance with the compositions and quantities of the bulk materials being delivered for stacking onto the mix bed, an aggregate composition of the bulk materials in respective sectors of the mix bed when said respective sectors are reclaimed.

In another aspect the present invention provides a computer readable storage medium for use in a computer used in a method of building a mix bed composed of many layers of variable bulk materials, from which slices of the bulk materials are reclaimed from time to time, said method including the steps of building a mix bed composed of many layers of variable bulk materials by stacking delivered variable bulk materials onto the mix bed at different locations in accordance with a schedule; analyzing the composition of the bulk materials being delivered for stacking onto the mix bed; measuring the quantities of the bulk materials being delivered for stacking onto the mix bed; and correlating the composition analyses and the quantity measurements with the different locations to which the bulk materials are being delivered for stacking, wherein the storage medium is configured so as to cause the computer to process the composition analyses and the quantity measurements with the location correlations to provide a real time data base of the current composition of the bulk materials in respective sectors of the mix bed.

Additional features of the present invention are described with reference to the detailed description of the preferred embodiments.

BRIEF DESCRIPTION OF THE DRAWING

FIG. 6 is a vertical sectional view of a mix bed taken in alignment with the direction of movement of the stacker, with the sectors being inclined at an angle corresponding to the angle at which slices are reclaimed from the mix bed.

FIG. 7A illustrates one predetermined pattern of building a non-circular mix bed, with which the systems and methods of the present invention are particularly useful.

FIG. 7B is a vertical sectional view of the mix bed of FIG. 7A, taken normal to the movement of the reclaimer.

FIG. 8A illustrates another predetermined pattern of building a mix bed, with which the systems and methods of the present invention are particularly useful.

FIG. 8B is a vertical sectional view of the mix bed of FIG. 8A, taken normal to the movement of the reclaimer.

DETAILED DESCRIPTION

Figure 5:
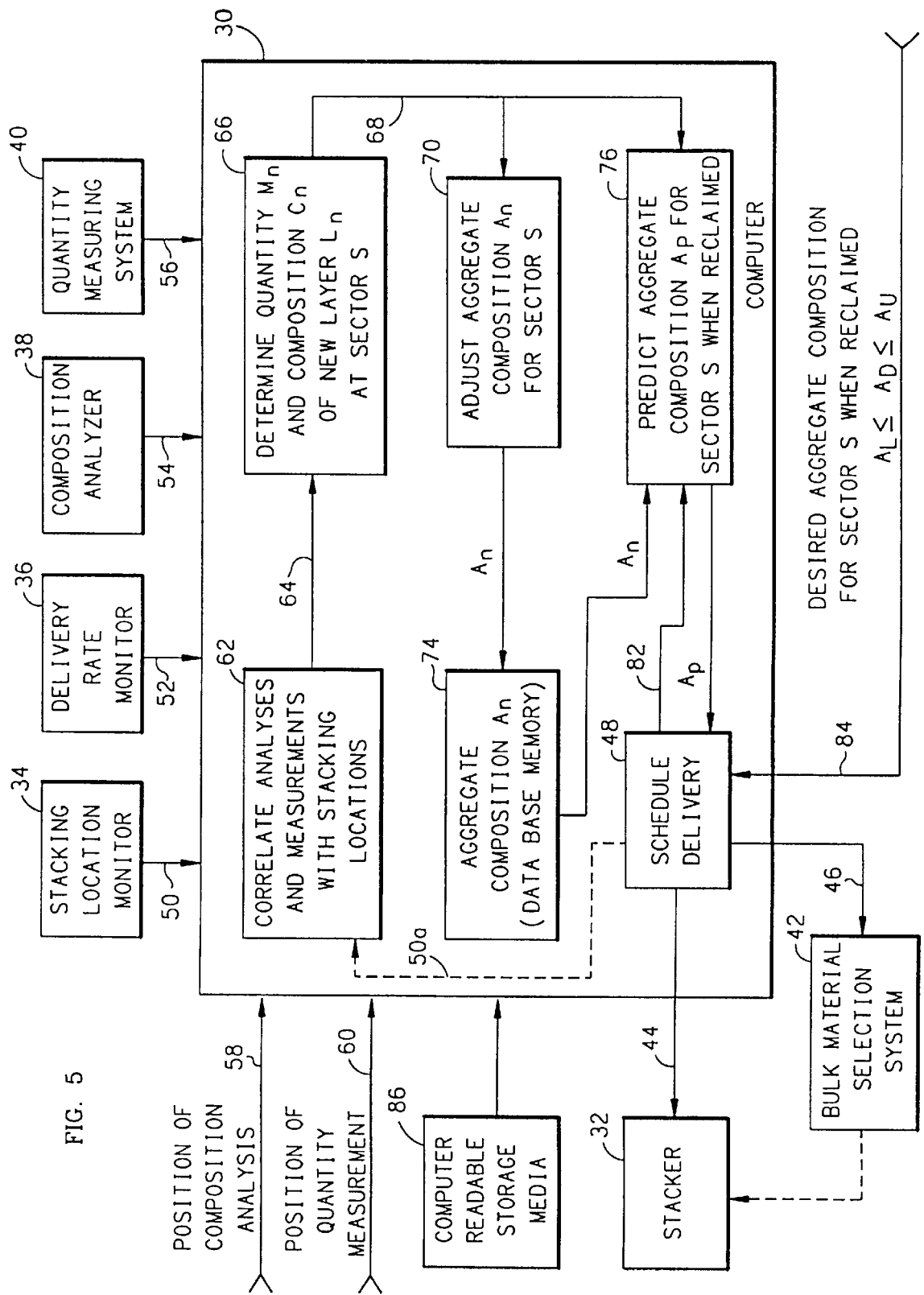
FIG. 5 is a block diagram of the systems and methods of the present invention.

Referring to FIG. 5, a preferred embodiment of the system according to the present invention for building a mix bed of variable bulk materials, from which slices of the bulk materials are reclaimed from time to time, includes a data processor or computer 30, a stacker 32, a stacker-location monitor 34, a delivery-rate monitor 36, an on-line, real-time bulk-material-composition analyzer 38, a quantity-measuring system 40, such as a conveyor-belt scale or some other mass flow measuring device, and a bulk-material-selection system 42. The bulk-material-selection system 42 selects different selected bulk materials for delivery to the stacker 32 from different sources either in response to a computer-generated material-selection schedule 46 or in accordance with selective operator control.

Stackers and stacker/reclaimers are well known in the art and may include a variety of radial stackers or homogenizing stores as well as other conveying and stacking equipment suitable for use in homogenizing and blending applications. The stacker 32 builds a mix bed composed of many layers of variable bulk materials by stacking delivered variable bulk materials onto the mix bed at different locations in accordance with a delivery-location schedule 44 generated by a "schedule delivery" routine 48 executed by the computer 30. The "schedule delivery" routine 48 also generates the material-selection schedule 46, which selects different bulk materials for delivery to the stacker 32 from different sources, and provides said schedule 46 to the bulk-material-selection system 42. An operator of the bulk-material-selection system 42 may override the material-selection schedule 46 provided by the "schedule delivery" routine 48. The operator of the bulk-material-selection system 42 may cause the bulk-material-selection system 42 to send an alternative delivery-location schedule 44a to the stacker thereby overriding the delivery-location schedule 44 provided by the "schedule delivery" routine 48.

The location of the stacker 32 is important for (a) determining the identity of the sector of the mix bed that is receiving the material and (b) providing the percent of completion of the current layer. The stacker-location monitor 34 continuously monitors the location of the stacker 32 and provides stacker-location signals 50 to the computer 30, which temporarily stores with respect to time stacker-location data indicated by the stacker-location signals 50. The stacker-location monitor 34 utilizes position sensors at known locations to monitor the position of the stacker. In an alternative embodiment, the stacker-location monitor 34 senses the direction and speed of movement of the stacker and processes the sensed data in relation to a known starting location to compute the monitored location of the stacker. Stacker location monitors are well known in the art and include laser measurement systems, i.e., optics-based systems, as well as electrical and electro-mechanical measurement systems. An exemplary commercial laser-based stacker-location measurement system is the Lasermeter LM4 available from Laser Measurement located in Midrand, South Africa.

The delivery-rate monitor 36 continuously monitors the rate at which the bulk material is being delivered to the stacker 32 for stacking onto the mix bed and provides delivery-rate signals 52 to the computer 30, which temporarily stores with respect to time delivery-rate data indicated by the delivery-rate signals 52. Preferably, the delivery rate monitor 36 measures the speed of the conveyor that is delivering the bulk material to location where the bulk material is stacked onto the mix bed. Appropriate delivery-rate monitors are commercially available and include optical, electrical, electro-mechanical, ultrasonic, and microwave flow rate instrumentation.

The bulk-material-composition analyzer 38 continuously analyzes the composition of the bulk materials being delivered for stacking onto the mix bed and provides real-time composition-analysis signals 54 to the computer 30, which temporarily stores with respect to time composition-analysis data indicated by the composition-analysis signals 54. Preferably the bulk material analyzer 38 performs PGNA analysis, although other real time analysis systems may be uses. Exemplary PGNAA systems and methods are described in U.S. Pat. Nos. 4,582,292 to Atwell et al. and 5,396,071 to Atwell et al. and in pending U.S. patent applications Nos. 08/492,575 and 08/822,075, now U.S. Pat. Nos. 5,732,115 and 5,825,030 respectively, the disclosures of which are incorporated herein by reference.

The quantity-measuring system 40 continuously measures the quantities of the bulk materials being delivered for stacking onto the mix bed and provides real-time quantity-measurement signals 56 to the computer 30, which temporarily stores with respect to time quantity-measurement data indicated by the quantity-measurement signals 56. Preferably, the quantity measuring system 40 includes a scale disposed within the conveyor assembly.

Data 58 indicating the position of the bulk material composition analyzer 38 and data 60 indicating the position of the quantity-measuring system 40 are entered into the computer 30. The quantity-measuring system 40 preferably travels with the output end of the stacker 32 such that the stacker-location monitor 34 will also provide the data 60 indicating the location of the quantity-measuring system 40. If, however, the location of the quantity measuring system 40 is independent of the output of the stacker 32 and is not at a fixed location, a separate location monitor (not shown) is provided in order to provide the data 60 indicating the position of the quantity-measuring system 40.

The computer 30 includes a data processor and at least one memory for storing control/monitor software and the analyzer software, as well as temporary storage for the raw and processed data. Interfaces including appropriate hardware and/or software (not shown) are provided for data communication and operator interface. In the preferred embodiment, the computer 30 is a personal computer (PC) type, such as an Intel PENTIUM-based PC having a 200 MHz CPU card with 64 MB of RAM, a large capacity (2.1 GB) hard drive for large data base archiving, a CD-ROM drive, and high resolution graphic monitor and printer. Due to potential dust contamination, the computer 30 should be housed in an enclosure suitable for the environment, which may include temperature and humidity control devices.

Figure 4:
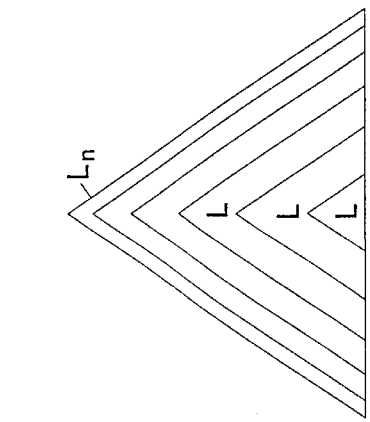
FIG. 4 is a vertical sectional view of a prior art circular mix bed, as shown in FIG. 3, taken in alignment with the circular direction of movement of the stacker.

The computer 30 determines the aggregate bulk material composition $A_n$ for respective different given sectors S of the mix bed. The given sectors S may be vertical, as shown in FIG. 4, but preferably are inclined from the vertical at an angle corresponding to the angle at which slices of bulk material are reclaimed from the mix bed, as shown in FIG. 6.

In order to account for the respective time delays from the times of generation of the composition-analysis signals 54 and the quantity-measurement signals 56 to the time of deposit onto the mix bed of the bulk material to which such signals 54, 56 relate, the computer 30 executes a routine 62 of processing the data indicated by the stacker-location signals 50, the delivery-rate signals 52, the composition analysis signals 54, and the quantity-measurement signals 56; the data 58 indicating the position of the bulk material composition analyzer 38; and the data 60 indicating the position of the quantity-measuring system 40 in order to correlate the composition-analysis data indicated by the composition-analysis signals 54 and the quantity-measurement data indicated by the quantity-measurement signals 56 with the different locations to which the bulk materials are being delivered for stacking and provides location-correlation data 64. In an alternative embodiment, data 50a indicating the scheduled stacker location, which is provided by the "schedule delivery" routine 48, is processed during execution of the correlation routine 62 in lieu of the data indicated by the stacker-location signals 50 provided by the stacker-location monitor 34. In such an alternative embodiment, the stacker-location monitor 34 may be omitted. The respective time delays from the times of generation of the composition-analysis signals 54 and the quantity-measurement signals 56 to the time of deposit onto the mix bed of the bulk material to which such signals relate are determined from the delivery-rate signals 52 and the known lengths of travel of the bulk material to the deposit location from the respective positions where the composition of the bulk material is analyzed and the quantity of the bulk material is measured.

The computer 30 executes a routine 66 of processing the correlation data 64 with the composition analyses data indicated by the composition analysis signals 54, and the quantity measurement data indicated the quantity-measurement signals 56 to determine the quantity $M_n$ and the composition $C_n$ in the different sectors S of a new layer $L_n$ of bulk material being applied to the mix bed as a result of the measured quantity $M_m$ and the analyzed composition $C_a$ of bulk material being stacked onto the mix bed at a given location by the stacker 32 and provides correlated data 68 indicating the quantity $M_n$ and the composition $C_n$ of the new layer $L_n$ thereby being applied to the mix bed at the different sectors S of the mix bed. $C_a$ may be the proportion of each element present, a quantity derived from elemental measurements, or any other measurable and useful quality obtainable from an on-line bulk material analyzer. The routine 66 compensates for characteristics of different types and/or sizes of materials within the bulk material stacked at a given location respectively tumbling different distances from the given location toward an edge of the mix bed by adjusting the quantity $M_n$ and the composition $C_n$ of the new layer L in the given sector S in accordance with such tumbling characteristics. The amount of such compensation is determined empirically by analyzing samples at the different distances from the given location.

The computer 30 executes a routine 70 of adjusting an aggregate bulk material composition $A_n$ for respective given sectors S stored in a data base memory 74 in accordance with the new composition and quantity data 68 and stores the adjusted aggregate bulk material composition data $A_n$ for all finished and unfinished sectors S in the data base memory 74 to provide a real time data base of the current composition of the bulk materials in the respective given sectors S of the mix bed. The routine 70 determines the aggregate bulk material composition $A_n$ for each given sector S in accordance with the following computation:

$$A_n = (C_1*M_1 + C_2*M_2 + \ldots C_n*M_n)/(M_1 + M_2 + \ldots M_n) \quad \text{(Eq. 1)}$$

where n is the number of layers in a sector at the time a computation is made. Separate computations are done for each measured element or quality, e.g. $A_{n1}$ for Calcium, $A_{n2}$ for Silicon, $A_{n3}$ for Iron, etc. Some composition qualities such as lime saturation factor (LSF), which is well known and widely used in the cement industry as a key measure of cement quality, can not be combined linearly. LSF is a particular ratio of calcium to iron, silicon, and aluminum. In such cases, in order to obtain the most accurate measure of the particular quality, the concentrations of each of the elements are combined as in equation 1, each being considered a separate quality, and then the LSF is computed for the aggregate sector or portion of the sector. A simple spread sheet calculation can detect circumstances when this must be done. Any composition quality which involves the ratio of sums of elemental compositions requires this type of treatment. It should be noted that sometimes a good approximation may be obtained by linear combination even when it is not strictly mathematically correct.

The computer 30 executes a prediction routine 76 of processing correlated current composition analyses and quantity measurements indicated by the data 68 with aggregate composition data $A_n$ from the real time data base 74 to predict, in accordance with the compositions and quantities of the bulk materials being delivered for stacking onto a given location of the mix bed, an aggregate composition $A_P$ of the bulk materials in the respective sectors S of the mix bed when the respective sectors S are reclaimed, and pursuant to such processing provides aggregate-composition predictions $A_P$ for the respective sectors S. In an alternative embodiment, the prediction routine 76 also processes delivery-schedule data 82 generated by the "schedule delivery" routine 48 to make the aggregate-composition prediction $A_P$ in further accordance with the compositions and quantities of the bulk materials scheduled for delivery for stacking onto the mix bed. The delivery-schedule data 82 combines the position schedule 44 and the selection schedule 46 provided by the "schedule delivery" routine 48.

During the "schedule delivery" routine 48, the computer 30 processes the calculated aggregate-composition predictions $A_P$ with data 84 indicating the desired aggregate compositions $A_D$ for the respective sectors S when the bulk material is reclaimed by comparing the calculated aggregated composition $A_P$ for a selected sector S with a desired aggregate composition $A_D$ for the selected sector S and, when the calculated predicted aggregated composition $A_P$ for the selected sector deviates form the desired aggregate composition $A_D$, the computer responds to aggregate-composition predictions $A_{Pu}$ indicating that stacking of a given delivered bulk material onto a given location of the mix bed would cause a given sector S of the mix bed including the given delivered bulk material delivered onto the given location to be of an undesired aggregate composition when the given sector S of the mix bed is reclaimed, by changing the position schedule 44 and/or the selection schedule 46 to thereby cause stacking of the given delivered bulk material onto the given location of the mix bed to be omitted.

$$A_L \leq A_D \leq A_U \quad \text{(Eq. 2)}$$

wherein $A_L$ and $A_U$ respectively represent the lower and upper limits of the desired range of the aggregate composition $A_D$. There may be several instances of equation 2 for each sector, there being one for each element or quality, e.g. LSF, silica ratio, iron modulus, etc.

The computer 30 calculates a corrective quantity and composition of bulk materials required for deposit onto the given location in order to correct said deviation. The composition $C_X$ of the undelivered bulk material required for causing the given sector to be of a desired aggregate composition $A_D$ when the given sector S of the mix bed is reclaimed is determined in accordance with the following:

$$A_D = C_D*M_D = C_C*M_C + C_X*M_X \quad \text{(Eq. 3)}$$

$$C_L \leq C_D \leq C_U \quad \text{(Eq. 4)}$$

wherein $C_D$ is the desired composition of the bulk material upon reclamation of the sector S, $M_D$ is the desired mass of the bulk material upon reclamation of sector S, $C_C$ is the current composition of the bulk material in sector S, $M_C$ is the current mass of the bulk material in sector S, $M_X$ is the mass of the undelivered bulk material for sector S, $C_L$ and $C_U$ respectively represent the lower and upper limits of the desired range of the composition $C_D$. As indicated above, qualities which are ratios of sums, such as LSF, must be arrived at by separately computing the percentage by weight of the constituent elements for the sector then computing the LSF for the sector S. If LSF, silica modulus and other nonlinear derived quantities are to be controlled, one may first solve a set of equations to determine the ranges of each of the element compositions that are required.

Controlling the optimal composition of materials when "optimal" is in terms of more than one quality parameter is complex, particularly when the controlled variables are heavily coupled, such as when the quality parameters are functions of the same set of oxides. Various searching strategies may be used to find the optimal solution for either the best blend of materials or the best single material for completion of a layer or sector subject to various practical constraints. One searching strategy is based on the Simplex method, which is linear programming technique to find an optimal point that is known to be at the intersection of two or more inequality constraints. Other searching strategies that my be used are based on Newton and quasi-Newton algorithms, which search on the basis of gradients. The core theory behind all of these multi-variable techniques can be found in the literature and computer libraries, such as the M++ Class Library. The OPTIM Optimization Module from Dyad Software may be used as the basis of a computer program for particular cases. There are also other computer software packages, such as Matlab, which may be used to assist in solving problems involving linear programming. Skilled artisans familiar with linear programming generally have the knowledge needed address problems of this type.

In order to determine the volume of the currently delivered bulk material that is to be omitted from stacking at the given location of the mix bed, the delivery schedule routine 48 calculates the maximum volume $V_M$ of corrective material needed to fully correct the composition of the given sector S, using the aggregate composition data $A_n$ from the real time data base 74 and the composition ranges of the available corrective bulk materials and causes the omitted quantity of the currently delivered bulk material to of at least such volume $V_M$.

The "schedule delivery" routine 48 responds further an undesired aggregate-composition predictions $A_{Pu}$ by changing the position schedule 44 and/or the selection schedule 46 to thereby cause at least one corrective bulk material to be stacked onto the given location of the mix bed subsequent to said omission in order to cause the given sector S of the mix bed to be of a desired aggregate composition $A_D$ when the given sector S of the mix bed is reclaimed.

The composition $C_X$ of corrective bulk material required for causing the given sector to be of a desired aggregate composition $A_D$ when the given sector S of the mix bed is reclaimed is determined in accordance with equations 3 and 4, taking into account the quantity of the bulk material that was omitted from stacking at the given location of the mix bed.

When material of the composition specified for correction of the mix bed sectors becomes available the stacker returns to the uncompleted sectors. As the stacker passes back and forth over the uncompleted region the composition of the delivered bulk material is continuously monitored in each sector to process the actual composition of the corrective material being stacked onto the mix bed rather than what was anticipated in accordance with the selection schedule 46. It is important that a margin of volume be left for further correction in case the corrective material is not exactly as anticipated.

The computer 30 is adapted for executing the aforementioned routines 48, 62, 66, 70, 76 by computer readable storage media 86 loaded into the computer 30 and configured for causing the computer 30 to execute such routines.

The present invention is also useful for selectively correcting aggregate-composition irregularities in one or more given sectors of both circular and non-circular mix beds without interrupting the continuous building of the mix bed.

One scheduled pattern of building a non-circular mix bed 88, with which the present invention is particularly useful, is shown in FIGS. 7A and 7B. Bulk material is reclaimed in slices from face 89 of the mix bed 88, as shown in FIG. 7B, with the reclaimer advancing in the directions shown by the arrow 90. Successively deposited layers of the mix bed 88 are arbitrarily numbered 1 through 11, as shown in FIG. 7B. The movement pattern of the stacker in depositing layer number 7 is shown in FIG. 7A by solid lines; and the movement pattern of the stacker in depositing layer number 8 is shown by dashed lines. Stacker position $pos_x$ (in the direction shown laterally in FIGS. 7A and 8A) provides the identity of the sector being traversed. Stacker position $pos_y$ provides a measure of the degree of completion of the layer as well as the number of stripes per layer. For this type of mix bed, the data base may be subdivided in the y direction as well as in the x direction, with the sectors thereby extending across only a portion of the width of the mix bed.

Another predetermined pattern of building a non-circular mix bed, with which the present invention is particularly useful is shown in FIGS. 8A and 8B. The scheduled pattern of building a non-circular mix bed 92, with which the present invention is particularly useful, is shown in FIGS. 8A and 8B. Bulk material is reclaimed in slices from face 93 of the mix bed 92, as shown in FIG. 8B, with the reclaimer advancing in the directions shown by the arrow 94. Successively deposited layers of the mix bed 88 are arbitrarily numbered 1 through 11, as shown in FIG. 8B. The movement pattern of the stacker in depositing layer number 7 is shown in FIG. 8A by solid lines; and the movement pattern of the stacker in depositing layer number 8 is shown by dashed lines.

Figure 1:
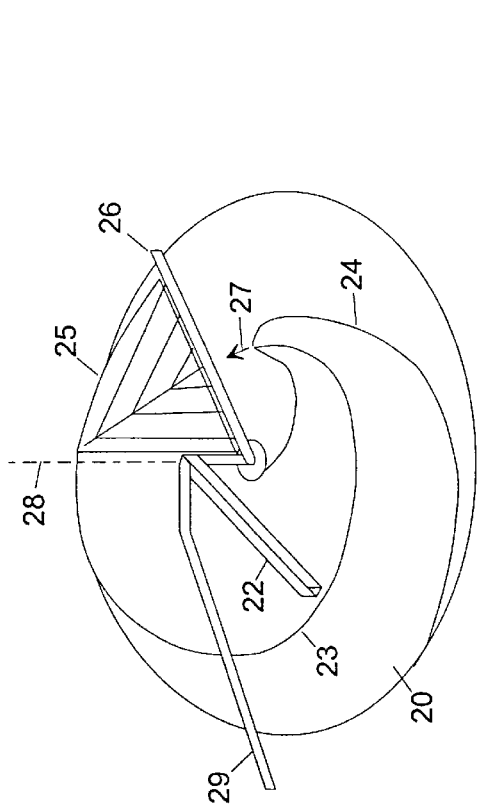
FIG. 1 illustrates the building of a prior art longitudinal mix bed and the reclaiming of bulk material therefrom.
Figure 2:
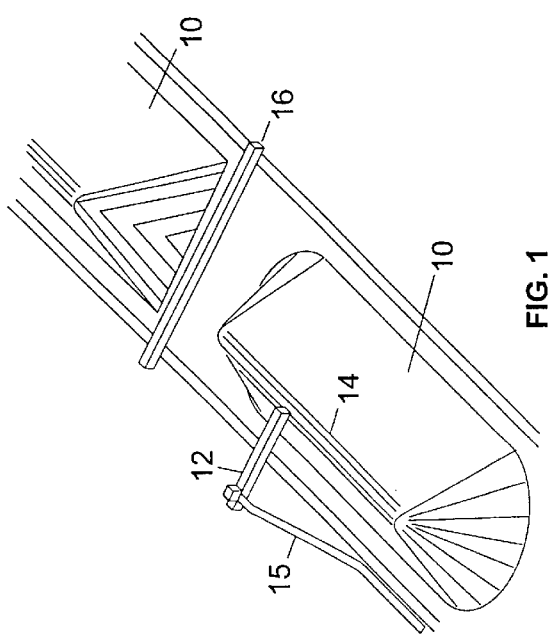
FIG. 2 is a vertical sectional view of a prior art mix bed, such as the longitudinal mix bed shown in FIG. 1 or a circular mix bed, taken normal to the movement of the stacker.
Figure 3:
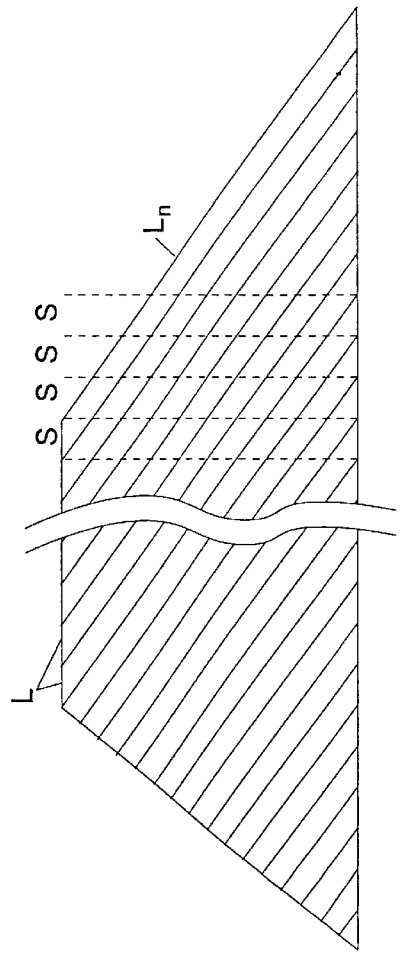
FIG. 3 illustrates continuous-mode building of a prior art circular mix bed and the reclaiming of bulk material therefrom.

The present invention is also useful for selectively correcting aggregate-composition irregularities in one or more given sectors of a longitudinal mix bed, such as shown in FIG. 1, wherein the stacker moves back and forth along the same ridge while depositing the bulk material.

The mix bed/sector/layer data bases can be thought of in terms of class objects. Each mix bed object consists of m sector objects and n layer objects. Also, the material in each sector object consists of material from r horizontal layer objects, s inclined layer objects, and t top layer objects. The mix bed, sector, and layer objects (i.e., data bases) are updated upon every new analysis. The attributes of each object (current tonnage, current chemistry, percent of completion, etc.) are available for use during layer prescription calculations and can also be monitored by the operator.

Two belt scales may be provided to provide quantity measurements for two different locations along the conveyor in certain applications in which there are variable time delays between the composition analyzer and the stacker. With two belt scales, correlation may be determined between either or both belt scale measurements and the bulk material analysis. A stacker status measurement indicates whether or not the stacker is moving (i.e., belt has material) or stopped (i.e., the belt is empty). The status measurement is used to improve the accuracy of the quantity measurement entered into the data base during periods of interrupted flow.

Other inputs are provided to the computer 30 by the operator, either in advance or in real-time, or are determined by default or through sensor information. For example, the layers may normally be inclined, but an operator could specify the number of horizontal bottom layers and top layers. This provides a flexible mix bed configuration that include any of the following, for example:

1. 8 Horizontal layers
2. 8 Inclined layers
3. 7 Inclined layers with 1 bottom horizontal layer
4. 6 Inclined layers with 2 bottom horizontal layer
5. 5 Inclined layers with 2 bottom horizontal layer and 1 top horizontal layer The operator must input the desired chemistry for the mix bed and the feasibility limits on prescribed chemistries. The feasibility limits on prescribed chemistries are usually in terms of percent oxides and represent the chemistry range of material that can be found in the available sources of bulk material.

Correlation between the bulk material analyses and quantity measurements is very important for accurate data base records. There is a first time delay $Dt_1$ between the quantity measurement of a given segment of bulk material by the belt scale on the bulk material analyzer conveyor belt and the analysis of the given segment of material by the bulk material analyzer. If belt speed is not constant, the time delay $Dt_1$ must be adjusted. Since a composition analysis usually requires some minimum interval of time, for example one minute, proper correlation at time $t=t_A$ calls for an integrated quantity measurement over said time interval for the same material as is being analyzed. There are additional delays between when the material passes through the analyzer and when the composition analysis signals are available for processing by the computer. Similarly there is a time delay from when the material passes over the weigh scale and when the quantity measurement signals are available to the computer. Furthermore, both the integration of the measurement data over such time interval and the computation of the analysis results from the composition measurement data introduce definable time delays. All of these delays must be determined and a combined time delay introduced with a lag filter so that the analysis interval and the weighing interval are properly synchronized.

It is also very important to compute the time delay $Dt_2$ between the time of the composition analysis and the time when the material is placed on the mix bed in order for the data base to be accurate. The conveyor belt speed will be variable, particularly during start-up and the stopping of the belt. The length of the conveyor belt from the position of the analyzer to the location where the material leaves the stacker to be placed on the mix bed also may be variable. In any event, the time delay $Dt_2$ may be computed from the known conveyor length and the belt speed. Although the details of how these time delays may be computed may vary from system to system, the objective is always to insure that for each material composition analysis, the analyzed chemical composition of the material is correlated with the ultimate location of the analyzed material in the mix bed.

Figure 9:
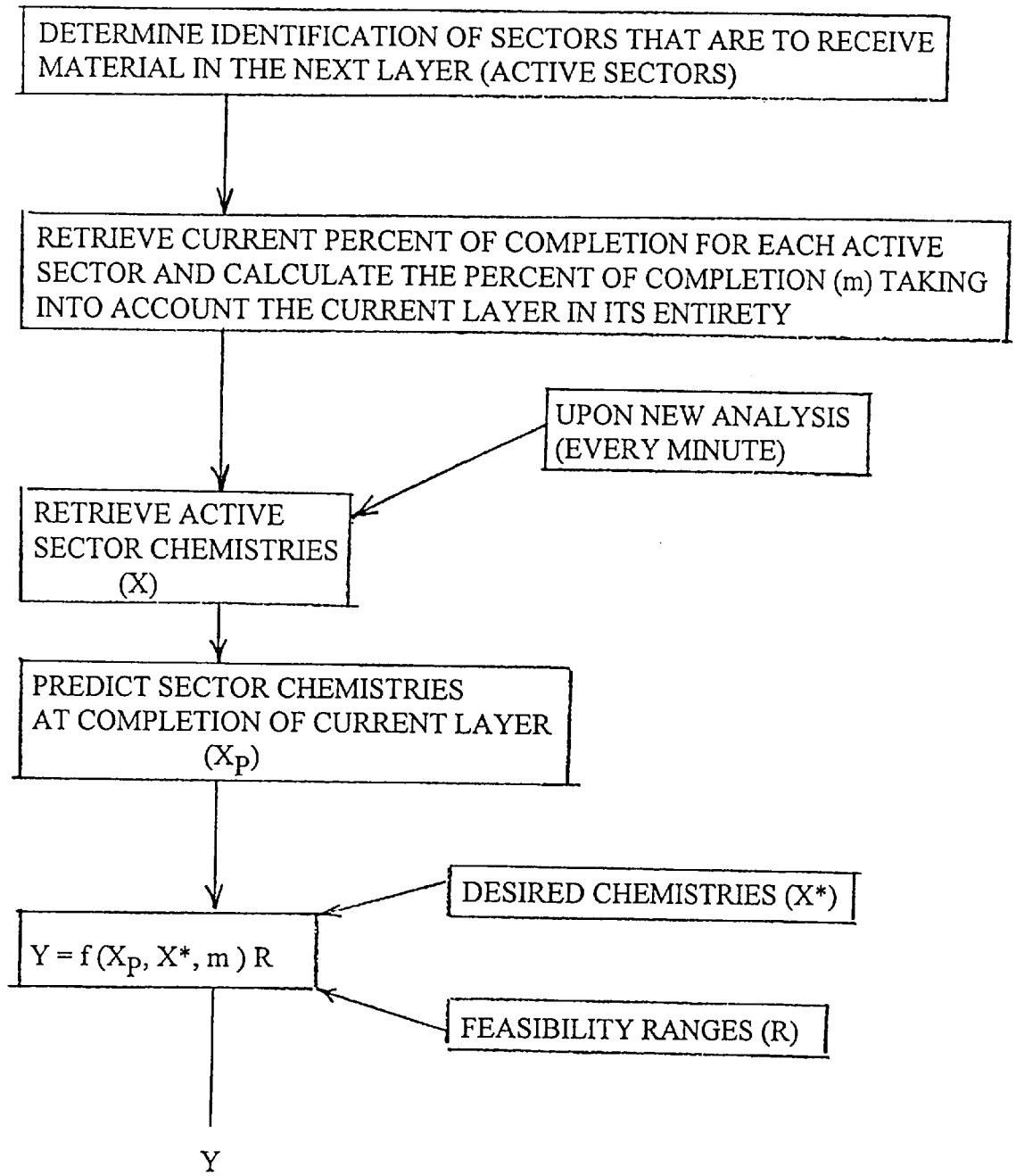
FIG. 9 shows an algorithm for calculating a prescription for the composition of a subsequent layer of the mix bed.

FIG. 9 is a flow diagram of an example of algorithm logic followed by the computer 30 to determine the chemistry prescription for the next layer. In this example it is assumed that a layer has a consistent chemistry. This may be useful where layer chemistry may not be changed quickly. In general the composition may be changed within a layer, thus allowing more freedom to precisely control sector composition. As was mentioned above, given the information described previously, the computer 30 updates the mix bed, sector, and layer objects upon every new analysis. The computer then has all the information needed to determine the quantity-weighted cumulative chemistry as well as percent completion for each sector that is to be traversed by the next deposited layer of bulk material. Finally, a prescription y for the next layer is calculated, the prescription y being a function of the chemistries and percent of completion of all sectors receiving material from the layer. The chemistries incorporate the entire present layer even though it may not yet be completed. Because the prescriptions are provided every minute, trending is possible, which can provide early determination of the next layer's preferred chemistry by observing convergence of the layer or sector chemistry with the objective. Assuming that a typical layer takes ten to fifteen minutes to build and the selected source material takes fifteen-to-twenty minutes to become available for feeding by the stacker once a prescription is acted on, the prescription may take effect one to three layers later. With the minute-to-minute prescriptions and assuming the chemistry of the present layer does not vary wildly, there should be sufficient time to determine the proper chemistry of the next layer while maintaining a efficient operation of supplying selected bulk material from the sources thereof.

The algorithm of FIG. 9 implements a strategy that assures that layer prescriptions are within the feasible limits as per the material available and (assuming the prescriptions are met) results in present and future sectors meeting desired chemistries.

For a given a set of sector quantities and qualities and a desired chemistry, which is shared by all sectors, and knowing the impact of the next layer on all sectors in terms of quantity, for a case in which the chemistry is nearly constant for each layer, two different approaches which may be used to optimize the prescription for n sectors of a future layer will be described. In one approach, the variable n provides an aggression factor and may or may not be equal to the number of sectors affected by the layer in question. In the second approach, the variable n is determined and used as a performance index to score how large a margin is achieved with the prescription. In both approaches, the algorithm of FIG. 9 calculates the prescriptions of several layers in the future. For example, if layer R is the next layer in need of a prescription, the algorithm bases the optimized prescription of layer R in part on the projected chemistries of layers S, T, and U. Similarly, the algorithm bases the optimized prescription of layer S in part on updated projected chemistries of layers T, U, and V. Two critical points concerning either approach are (a) all prescription and projected chemistries are constrained to the feasibility chemistry as provided by the operator, and (b) it is assumed that success is a discrete measure. For example, if a sector's chemistry falls within desired limits, then success is TRUE, otherwise success is FALSE.

In the first strategy, the computer 30 is programmed to provide the prescription that allows future prescriptions to maximize their distance from the feasibility limits. In the second approach, the computer 30 is programmed to achieve "perfect chemistry" for each sector in the horizon and the computer 30 determines how many layers into the future (n) it takes before the required layer chemistry violates the feasibility limits. For both strategies, there remains the question of how to weight a prescription in terms of the sectors that are directly affected by the layer. For example, layer R may complete Sector 6, but Sector 7 has one additional layer to go, Sector 8 has two additional layers, etc. Since Sector 6 has one layer left for completion, it may be difficult, and in some cases impossible, to complete the sector within the desired range of chemistry. In general, as a given sector approaches its feasibility limits it must be given a greater weighting to give it the best opportunity to be kept within the feasibility limits. These limits depend upon the number of layers yet to be placed in the sector, how close the composition is to the defined constraints, and the corrective material available. In some cases if a sector approaches or exceeds the feasibility limit it may be necessary to give that sector most or even all of the weighting in order to stay within, or at least near, the desired constraints. The limits of the range of desired chemistry provide the constraints for the optimization process for the future layers.

A preferred optimization process utilizes a searching algorithm based on the Simplex method. This method allows the algorithm to quickly identify all extremized feasibility points. Extremized feasibility points are those along the outer surface of the feasibility space. The fundamental theory behind the Simplex method is that the optimal solution is located on that surface. This can be explained as follows: Imagine a volume that is constrained by a set of parameters (chemistries in this case). All points within that volume make up the "solution space" and all are called feasible because they satisfy all constraints. The Simplex method states that the optimal solution necessarily extremizes at least one constraint and, therefore, is located on the volume's surface. The searching algorithm consists of a series of linear algebra steps called pivoting, in which the connections between extremized feasibility points are traveled in search of all such points that satisfy a criterion. Once the list of feasibility points are identified, sorting takes place to identify the single optimized prescription.

Figure 10:
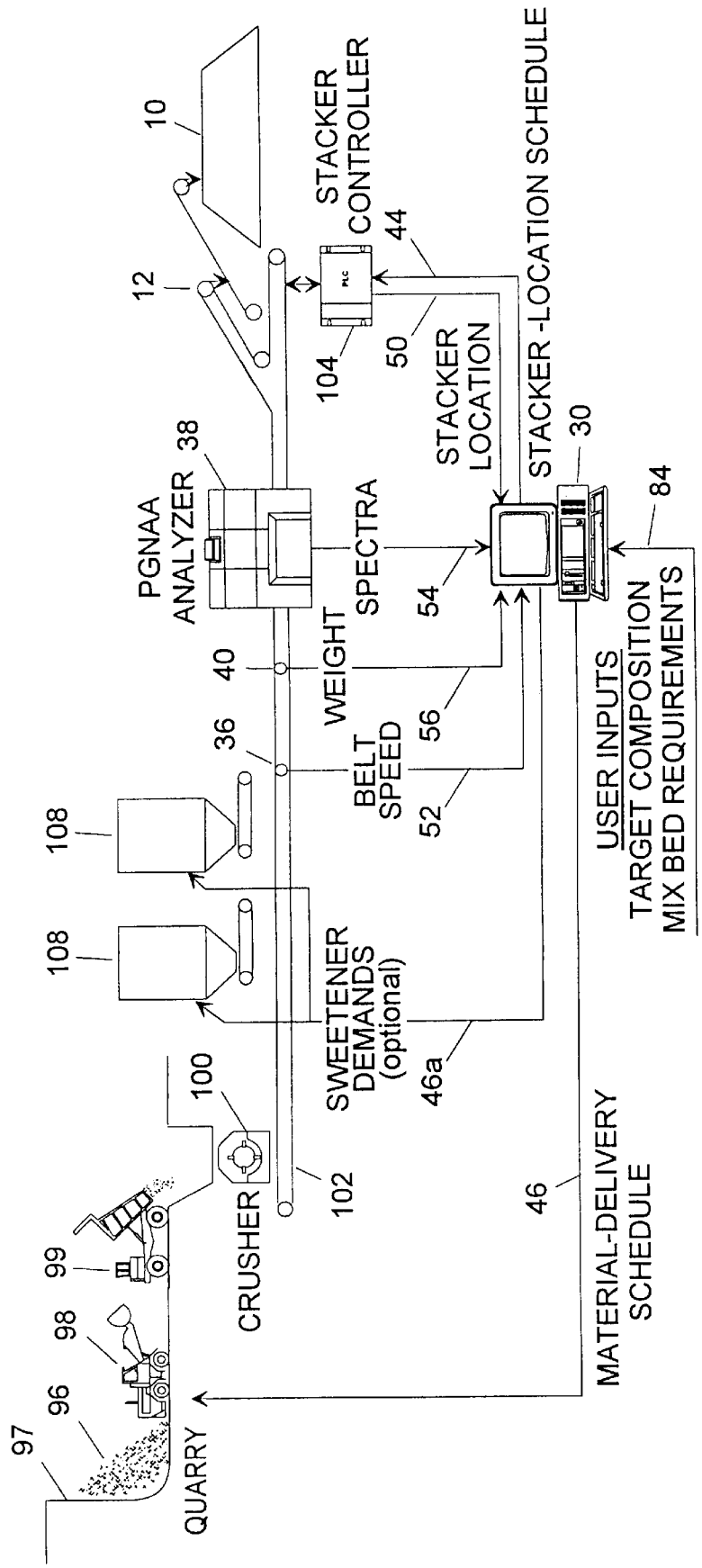
FIG. 10 illustrates the use of the present invention.

FIG. 10 illustrates the use of the present invention when building a mix bed 10 with bulk material 96 obtained from a quarry 97. The bulk material 96 is delivered by vehicles 98, 99 from the quarry 97 to a crusher 100, from which the crushed bulk material is transported by a conveyor 102 to a stacker 12. Enroute to the stacker 12, the bulk material 96 is weighed by a belt scale 40 adjacent the conveyor belt 102 and the composition of the bulk material is analyzed by a PGNAA analyzer 38, through which the belt 102 passes. Quantity measurement (weight) signals 56 from the belt scale 40 and composition analysis (spectra) signals 54 from the analyzer 38 are provided to the computer 30, where they are processed with delivery-rate (belt-speed) signals 52 from the delivery rate monitor 36, stacker location signals 50 from a stacker controller 104 and user input signals 84 specifying a target composition quality and the mix bed requirements to thereby provide a delivery-location schedule 44 to the stacker controller 104 and a material-selection schedule 46 to the quarry 97, as described above with reference to FIG. 5. As an option, a sweetener-demand schedule 46a may be provided to sweetener bins 108, from which different bulk materials are selectively provided onto the conveyor belt 102 in order to provide the desired mix of bulk materials for stacking onto the mix bed 10.

The advantages specifically stated herein do not necessarily apply to every conceivable embodiment of the present invention. Further, such stated advantages of the present invention are only examples and should not be construed as the only advantages of the present invention. While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

We claim:

1. A system for building a mix bed of variable bulk materials, from which slices of the bulk materials are reclaimed from time to time, comprising means for building a mix bed composed of many layers of variable bulk materials by stacking delivered variable bulk materials onto the mix bed at different locations in accordance with a schedule;

means for analyzing the composition of the bulk materials being delivered for stacking onto the mix bed;

means for measuring the quantities of the bulk materials being delivered for stacking onto the mix bed;

means for correlating the composition analyses and the quantity measurements with the different locations to which the bulk materials are being delivered for stacking; and means adapted for processing the composition analyses and the quantity measurements with the location correlations to predict, in accordance with the compositions and quantities of the bulk materials being delivered for stacking onto the mix bed, an aggregate composition of the bulk materials in respective sectors of the mix bed when said respective sectors are reclaimed.

2. A system according to claim 1, further comprising means adapted for responding to aggregate-composition predictions indicating that stacking of a given delivered bulk material onto a given location of the mix bed would cause a given sector of the mix bed including the given delivered bulk material delivered onto the given location to be of an undesired aggregate composition when the given sector of the mix bed is reclaimed, by causing stacking of the given delivered bulk material onto the given location of the mix bed to be omitted.

3. A system according to claim 2, further comprising means adapted for responding to said undesired-aggregate-composition prediction by causing at least one corrective bulk material to be stacked onto said given location of the mix bed subsequent to said omission in order to cause said given sector of the mix bed to be of a desired aggregate composition when said given sector of the mix bed is reclaimed.

4. A system according to claim 1, wherein said sectors are approximately vertical.

5. A system according to claim 1, wherein said sectors are at an angle corresponding to the angle at which said slices are reclaimed.

6. A system for building a mix bed of variable bulk materials, from which slices of the bulk materials are reclaimed from time to time, comprising means for building a mix bed composed of many layers of variable bulk materials by stacking delivered variable bulk materials onto the mix bed at different locations in accordance with a schedule;

means for analyzing the composition of the bulk materials being delivered for stacking onto the mix bed;

means for measuring the quantities of the bulk materials being delivered for stacking onto the mix bed;

means for correlating the composition analyses and the quantity measurements with the different locations to which the bulk materials are being delivered for stacking; and means adapted for processing the composition analyses and the quantity measurements with the location correlations to provide a real time data base of the current composition of the bulk materials in respective sectors of the mix bed.

7. A system according to claim 6, further comprising means adapted for compensating for characteristics of different types and sizes of materials within the bulk material stacked at a given location respectively tumbling different distances from said given location toward an edge of the mix bed by adjusting said real time data base in accordance with said tumbling characteristics.

8. A system according to claims 6, further comprising means adapted for processing current composition analyses and current quantity measurements with current location correlations and the real time data base to predict, in accordance with the compositions and quantities of the bulk materials being delivered for stacking onto the mix bed, an aggregate composition of the bulk materials in said respective sectors of the mix bed when said respective sectors are reclaimed.

9. A system according to claim 6, wherein said sectors are approximately vertical.

10. A system according to claim 6, wherein said sectors are at an angle corresponding to the angle at which said slices are reclaimed.

11. A system for use in a method of building a mix bed composed of many layers of variable bulk materials, from which slices of the bulk materials are reclaimed from time to time, said method including the steps of building a mix bed composed of many layers of variable bulk materials by stacking delivered variable bulk materials onto the mix bed at different locations in accordance with a schedule; analyzing the composition of the bulk materials being delivered for stacking onto the mix bed; measuring the quantities of the bulk materials being delivered for stacking onto the mix bed; and correlating the composition analyses and the quantity measurements with the different locations to which the bulk materials are being delivered for stacking, said system comprising means adapted for processing the composition analyses and the quantity measurements with the location correlations to predict, in accordance with the compositions and quantities of the bulk materials being delivered for stacking onto the mix bed, an aggregate composition of the bulk materials in respective sectors of the mix bed when said respective sectors are reclaimed; and means adapted for responding to aggregate-composition predictions indicating that stacking of a given delivered bulk material onto a given location of the mix bed would cause a given sector of the mix bed including the given delivered bulk material delivered onto the given location to be of an undesired aggregate composition when the given sector of the mix bed is reclaimed, by causing stacking of the given delivered bulk material onto the given location of the mix bed to be omitted.

12. A system according to claim 11, further comprising means adapted for responding to said undesired-aggregate-composition prediction by causing at least one corrective bulk material to be stacked onto said given location of the mix bed subsequent to said omission in order to cause said given sector of the mix bed to be of a desired aggregate composition when said given sector of the mix bed is reclaimed.

13. A system according to claim 11, wherein said sectors are approximately vertical.

14. A system according to claim 11, wherein said sectors are at an angle corresponding to the angle at which said slices are reclaimed.

15. A method of building a mix bed of variable bulk materials, from which slices of the bulk materials are reclaimed from time to time, comprising the steps of:

(a) building a mix bed composed of many layers of variable bulk materials by stacking delivered variable bulk materials onto the mix bed at different locations in accordance with a schedule;

(b) analyzing the composition of the bulk materials being delivered for stacking onto the mix bed;

(c) measuring the quantities of the bulk materials being delivered for stacking onto the mix bed;

(d) correlating the composition analyses and the quantity measurements with the different locations to which the bulk materials are being delivered for stacking; and (e) processing the composition analyses and the quantity measurements with the location correlations to predict, in accordance with the compositions and quantities of the bulk materials being delivered for stacking onto the mix bed, an aggregate composition of the bulk materials in respective sectors of the mix bed when said respective sectors are reclaimed.

16. A method according to claim 15, further comprising the step of:

(f) responding to aggregate-composition predictions indicating that stacking of a given delivered bulk material onto a given location of the mix bed would cause a given sector of the mix bed including the given delivered bulk material delivered onto the given location to be of an undesired aggregate composition when the given sector of the mix bed is reclaimed, by causing stacking of the given delivered bulk material onto the given location of the mix bed to be omitted.

17. A method according to claim 16, further comprising the step of:

(g) responding to said undesired-aggregate-composition prediction by causing at least one corrective bulk material to be stacked onto said given location of the mix bed subsequent to said omission in order to cause said given sector of the mix bed to be of a desired aggregate composition when said given sector of the mix bed is reclaimed.

18. A method according to claim 15, wherein said sectors are approximately vertical.

19. A method according to claim 15, wherein said sectors are at an angle corresponding to the angle at which said slices are reclaimed.

20. A method of building a mix bed of variable bulk materials, from which slices of the bulk materials are reclaimed from time to time, comprising (a) building a mix bed composed of many layers of variable bulk materials by stacking delivered variable bulk materials onto the mix bed at different locations in accordance with a schedule;

(b) analyzing the composition of the bulk materials being delivered for stacking onto the mix bed;

(c) measuring the quantities of the bulk materials being delivered for stacking onto the mix bed;

(d) correlating the composition analyses and the quantity measurements with the different locations to which the bulk materials are being delivered for stacking; and (e) processing the composition analyses and the quantity measurements with the location correlations to provide a real time data base of the current composition of the bulk materials in respective sectors of the mix bed.

21. A method according to claim 20, further comprising the step of:

(f) compensating for characteristics of different types and or sizes of materials within the bulk material stacked at a given location respectively tumbling different distances from said given location toward an edge of the mix bed by adjusting said real time data base in accordance with said tumbling characteristics.

22. A method according to claims 20, further comprising the step of:

(f) processing current composition analyses and current quantity measurements with current location correlations and the real time data base to predict, in accordance with the compositions and quantities of the bulk materials being delivered for stacking onto the mix bed, an aggregate composition of the bulk materials in said respective sectors of the mix bed when said respective sectors are reclaimed.

23. A method according to claim 20, wherein said sectors are approximately vertical.

24. A method according to claim 20, wherein said sectors are at an angle corresponding to the angle at which said slices are reclaimed.

25. A computer readable storage medium for use in a computer used in a method of building a mix bed composed of many layers of variable bulk materials, from which slices of the bulk materials are reclaimed from time to time, said method including the steps of building a mix bed composed of many layers of variable bulk materials by stacking delivered variable bulk materials onto the mix bed at different locations in accordance with a schedule; analyzing the composition of the bulk materials being delivered for stacking onto the mix bed; measuring the quantities of the bulk materials being delivered for stacking onto the mix bed; and correlating the composition analyses and the quantity measurements with the different locations to which the bulk materials are being delivered for stacking, wherein the storage medium is configured so as to cause the computer to process the composition analyses and the quantity measurements with the location correlations to predict, in accordance with the compositions and quantities of the bulk materials being delivered for stacking onto the mix bed, an aggregate composition of the bulk materials in respective sectors of the mix bed when said respective sectors are reclaimed.

26. A storage medium according to claim 25, further configured so as to cause the computer to respond to aggregate-composition predictions indicating that stacking of a given delivered bulk material onto a given location of the mix bed would cause a given sector of the mix bed including the given delivered bulk material delivered onto the given location to be of an undesired aggregate composition when the given sector of the mix bed is reclaimed, by causing stacking of the given delivered bulk material onto the given location of the mix bed to be omitted.

27. A storage medium according to claim 26, further configured so as to cause the computer to respond further to said undesired-aggregate-composition prediction by causing at least one corrective bulk material to be stacked onto said given location of the mix bed subsequent to said omission in order to cause said given sector of the mix bed to be of a desired aggregate composition when said given sector of the mix bed is reclaimed.

28. A system according to claim 25, wherein said sectors are approximately vertical.

29. A storage medium according to claim 25, wherein said sectors are at an angle corresponding to the angle at which said slices are reclaimed.

30. A computer readable storage medium for use in a computer used in a method of building a mix bed composed of many layers of variable bulk materials, from which slices of the bulk materials are reclaimed from time to time, said method including the steps of building a mix bed composed of many layers of variable bulk materials by stacking delivered variable bulk materials onto the mix bed at different locations in accordance with a schedule; analyzing the composition of the bulk materials being delivered for stacking onto the mix bed; measuring the quantities of the bulk materials being delivered for stacking onto the mix bed; and correlating the composition analyses and the quantity measurements with the different locations to which the bulk materials are being delivered for stacking, wherein the storage medium is configured so as to cause the computer to process the composition analyses and the quantity measurements with the location correlations to provide a real time data base of the current composition of the bulk materials in respective sectors of the mix bed.

31. A storage medium according to claim 30, further configured so as to cause the computer to process current composition analyses and current quantity measurements with current location correlations and the real time data base to predict, in accordance with the compositions and quantities of the bulk materials being delivered for stacking onto the mix bed, an aggregate composition of the bulk materials in said respective sectors of the mix bed when said respective sectors are reclaimed.

32. A system according to claim 30, wherein said sectors are approximately vertical.

33. A storage medium according to claim 30, wherein said sectors are at an angle corresponding to the angle at which said slices are reclaimed.

34. A system for building a mix bed of variable bulk materials, from which slices of the bulk materials are reclaimed from time to time, comprising a stacker for feeding bulk materials and for depositing the fed bulk materials at a plurality of different locations of a mix bed to sequentially form a plurality of stacked layers of bulk materials across the mix bed;

a stacker locator for providing a location signal indicating the location at which the stacker is depositing the bulk material;

a composition analyzer for determining a composition of the bulk materials being fed by the stacker and for providing a composition signal indicating said determined composition;

a quantity measurement system for measuring a quantity of the bulk materials being fed by the stacker and for providing a quantity signal indicating said measured quantity; and a computer coupled to the stacker locator, the composition analyzer and the quantity measurement system for receiving the location signal, the composition signal and the quantity signal, wherein the computer is adapted for processing the location signal, the composition signal and the quantity signal to correlate the location at which the stacker deposits the bulk material with the composition and quantity of the bulk material deposited at said location and to calculate a predicted aggregate composition of the bulk materials within a selected sector of the mix bed formed by deposit of bulk material at said location.

35. A system according to claim 34, wherein the computer is further adapted for comparing the calculated aggregated composition for the selected sector with a desired aggregate composition for the selected sector and, when the calculated predicted aggregate composition for the selected sector deviates from the desired aggregate composition, for communicating a signal that causes the stacker to omit deposit of the fed bulk materials onto said location of the mix bed during deposition of at least one subsequent layer onto the mix bed.

36. A system according to claim 35, wherein the computer is further adapted for calculating a corrective quantity and composition of bulk materials required for deposit onto said location in order to correct said deviation and for communicating a signal that causes the stacker to deposit the corrective quantity and composition of bulk materials onto said location of the mix bed where deposit was omitted.

* * * * *

UNITED STATES PATENT AND TRADEMARK OFFICE
CERTIFICATE OF CORRECTION

PATENT NO : 5,959,870
DATED : SEPTEMBER 28, 1999
INVENTOR(S) : MICHAEL JACK HURWITZ ET AL.

It is certified that error appears in the above-identified patent and that said Letters Patent is hereby corrected as shown below:

Column 18, line 65, "or" should be deleted.

Signed and Sealed this

Sixth Day of June, 2000

*Attest:*

Q. TODD DICKINSON

*Attesting Officer*   *Director of Patents and Trademarks*